United States Patent [19]

Green et al.

[11] Patent Number: 5,231,175
[45] Date of Patent: Jul. 27, 1993

[54] PROCESS FOR THE PREPARATION OF 3'- OR 2'-HALO-SUBSTITUTED-2',3'-DIDEOXYNUCLEOSIDES

[75] Inventors: Kenneth E. Green, Pearl River, N.Y.; David M. Blum, Upper Saddle River, N.J.; Michael P. Trova, Salisbury Mills, N.Y.

[73] Assignee: American Cyanamid Company, Stamford, Conn.

[21] Appl. No.: 833,191

[22] Filed: Feb. 10, 1992

[51] Int. Cl.$^5$ .............................................. C07H 1/00
[52] U.S. Cl. .................................. 536/26.1; 536/26.8; 536/27.14
[58] Field of Search ..................... 536/23, 26.1, 26.8

[56] References Cited

U.S. PATENT DOCUMENTS 3,775,397 11/1973 Etzold et al. ..................... 536/23
3,855,307 12/1974 Rony et al. ....................... 568/454

Primary Examiner—Johnnie R. Brown
Assistant Examiner—J. Oliver Wilson
Attorney, Agent, or Firm—Kenneth J. Dow

[57] ABSTRACT

A process for the preparation of 2' and 3'-(halo-substituted)-2',3'-dideoxy nucleosides by reacting a protected anhydrothymidine compound with a halogenating composition containing a transition metal or lanthanide compound.

20 Claims, No Drawings

PROCESS FOR THE PREPARATION OF 3'- OR 2'-HALO-SUBSTITUTED-2',3'-DIDEOXYNUCLEOSIDES

BACKGROUND OF THE INVENTION

1. Field of the Invention

The present invention is directed to a novel process for the synthesis of 3'-(halo-substituted)-2',3'-dideoxynucleosides and 2'-(halo-substituted)-2',3'-dideoxynucleosides from the corresponding anhydro-dideoxynucleoside counterparts.

2. Description of the Prior Art

Acquired Immunodeficiency Syndrome (AIDS), recognized as a systemic immunosuppressive disorder, is an infectious disease caused by a retrovirus termed human immunodeficiency virus (HIV). Since HIV is a retrovirus, viral reverse transcriptase appears to be a selective target for antiviral agents. Accordingly, a number of different reverse transcriptase inhibitors having different chemical structures have been reported to be active against HIV replication in vitro and in vivo.

Of these reverse transcriptase inhibitors, the 2',3'-dideoxyribonucleosides in particular are reported to have significant inhibitory activity against HIV in vitro (R. Dagani, Chem. and Eng. News, 41–49, Nov. 23, 1987; E. De Clercq, A. Van Aerschot, P. Herdewijn, M. Baba, R. Pauwels and J. Balzarini Nucleosides and Nucleotides, 8 (5 and 6), 659–671 (1989); A. Van Aerschot, P. Herdewijn, J. Balzarini, R. Pauwels and E. De Clercq, J. Med. Chem. 32, 1743–1749 (1989)).

Among the 2',3'-dideoxyribonucleoside products reported, 3'-azido-2',3'-dideoxythymidine (AZT), and 3'-deoxy-3'-fluorothymidine (also referred to as 2',3'-dideoxy-3'-fluorothymidine or FLT) in particular show selective anti-HIV-1 activity. The compound 3'-azido-2',3'-dideoxythymidine (AZT) is being sold commercially as a potent inhibitor of HIV-induced cytopathogenicity. However, 3'-deoxy-3'-fluorothymidine is reported to have increased activity over AZT (Balzarini, J., et al., Biochem. Pharmacol. 1988, 37, 2847; P. Herdewijn, J., et al., J. Med. Chem. 30, 1270–1278 (1987)). Accordingly, the compound 3'-deoxy-3'-fluorothymidine (FLT) and other 2' or 3' -fluorosubstituted deoxynucleosides are in particular interest as possible agents for the treatment for AIDS.

The synthesis of FLT is known from G. Etzold, R. Hintsche, G. Kowollik and P. Langen, Tetrahedron 27 (1971) pp. 2463–2472. They describe the reaction of 2,3'-Anhydro-1-(2-deoxy-β-D-xylofuranosyl)thymine with HF using $AlF_3$ as a catalyst at 150°–170° to obtain the product at 28% yield. They also describe its preparation by the reaction of 3'-0-mesyl-thymidine with $KHF_2$ or $NH_4F$ at 190° to obtain the product at 14% yield. In another reference, the authors synthesized 3'-deoxy-3'-fluorothymidine from 2,3'-anhydro-1-(2-deoxy-5-0-mesyl-β-D-threo-pentofuranosyl)thymine using HF-$AlF_3$. (J. Prakt. Chem., 315, 895 (1973).

In U.S. Pat. No. 3,775,397 the same authors report the preparation of 3'-deoxy-3'-fluorothymidine by heating the 2,3'-anhydro-1-(2-deoxy-β-D-xylofuranosyl)thymine with 30 cm.[3] of a 4–6% solution of HF in anhydrous dioxane in a sealed vessel at 90° C. to obtain the product at yields of up to 46%. Attempts to reproduce these procedures by the present inventors have not produced any appreciable amounts of the product, however.

Other closely related compounds have been fluorinated using diethylaminosulfur trifluoride (DAST). (See A. Van Aerschot, P. Herdewijn, J. Balgarini, R. Pauwels and E. DeClerq., J. Med. Chem. 32, 1743–1749 (1989))

In pending application Ser. No. 563,596 filed Aug. 6, 1990, an improved process for the preparation of 2' and 3'-(halo-substituted)-2',3'-dideoxy nucleosides by reacting a protected anhydrothymidine compound with a halogenating composition containing a substituted organoaluminum compound which exhibits greater solubility in conventional solvents than $AlF_3$ is disclosed.

Surprisingly, it has been discovered that the use of a transition or lanthanide compound in the presence of HF produces 2' or 3'-(fluoro-substituted)-dideoxynucleosides.

SUMMARY OF THE INVENTION

This invention embodies the general concept of using lanthanide or transition metal compounds to enhance the ability of nucleophiles to be substituted on nucleosides.

In particular, this invention is directed to an improved process for preparing 3'-(halo-substituted)-2',3'-dideoxynucleosides and 2'-(halo-substituted)-2',3'-dideoxynucleosides by reacting a protected anhydrothymidine compound with a lanthanide or transition metal compound.

More specifically, the invention is directed to an improved process for preparing 2'or 3'-(halosubstituted)-2',3'-di-deoxynucleosides selected from those of formulae:

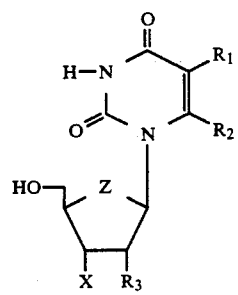

I

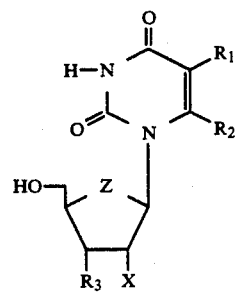

II wherein
Z is oxygen or $CH_2$;
$R_1$ and $R_2$ may be the same or different and are selected from hydrogen, lower alkyl and halogen,
$R_3$ is selected from hydrogen and halogen; and X is a halogen;
which process comprises the steps of:
(A) reacting a compound of Formula (1a) or (1b)

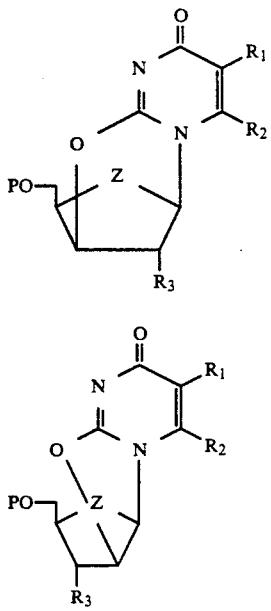

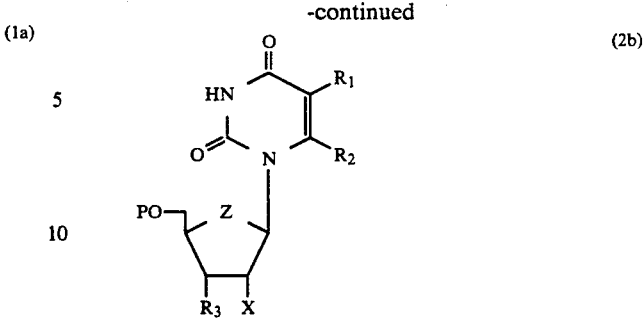

wherein R₁, R₂, and R₃ are as hereinbefore defined and P is hydrogen or a suitable protecting group which may be selected from those consisting of triphenylmethyl, methoxytriphenylmethyl, acetyl, pivaloyl, methanesulfonyl or trialkyl-silyl with a reagent of the formula:

H—X wherein X is a halogen in the presence of an additional reagent of the formula:

M—Y wherein M is selected from the group known as the transition or lanthanide metals consisting of scandium, titanium, vanadium, chromium, manganese, iron, cobalt nickel, copper, zinc, yttrium, zironium, niobium, molybdenum, technetium, ruthenium, rhodium, palladium, silver, cadmium, lanthanum, hafnium, tantalum, tungsten, rhenium, osmium, iridium, platinum, gold, mercury, actinium, rutherfordium, hahnium, cerium, praseodymium, neodymium, promethium, samarium, europium, gadolinium, terbium, dysprosium, holmium, erbium, thulium, ytterbium, lutetium; y is $(C_1-C_{10})$ branched or unbranched alkyl, halogen or acetylacetonate, to yield a protected intermediate of the Formula (2a) or (2b),

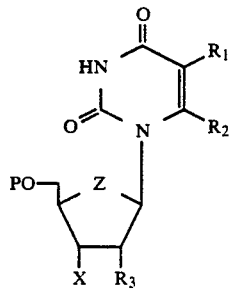

and then (B) where P is other than hydrogen, removing the protecting group P to give the 3'-(halo-substituted)2',3'-dideoxynucleosides or 2'-(halo-substituted)-2',3'-dideoxynucleosides. When P is hydrogen, removal of the protecting group P is unnecessary.

DETAILED DESCRIPTION OF THE INVENTION

The process for preparing the 2'or 3'-(halo-substituted)2',3'-dideoxynucleosides may conveniently be summarized by the following reaction sequence of Scheme I.

In this reaction, the protected anhydronucleoside (1a) or (1b), is reacted in Step (A) to give the protected substituted nucleosides (2a) or (2b) which can then be converted in Step (B) to the deprotected 3'-(substituted)2',3'-dideoxynucleoside (3a) and the 2'-(substituted)2',3'-dideoxynucleoside (3b) by reported procedures. Scheme I is as follows:

Scheme I

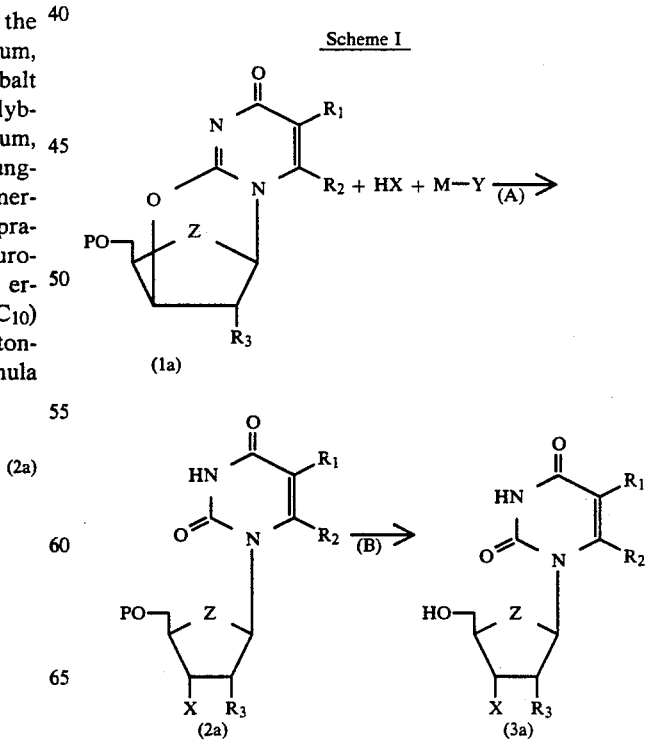

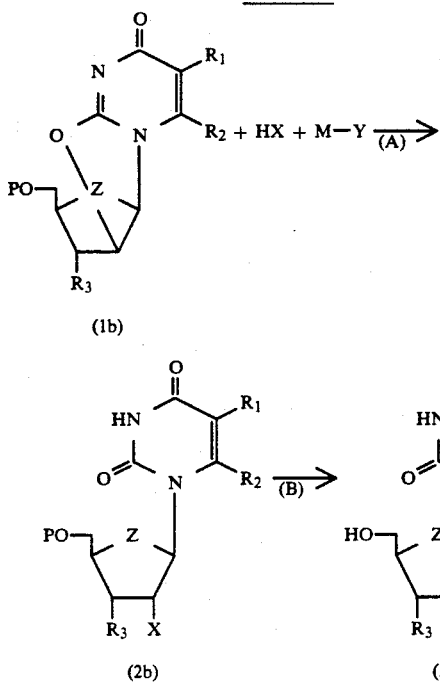

Referring to Scheme I, Step (A) illustrates the reaction between an appropriately substituted reagent H—X and an anhydronucleoside (1a) or (1b) in the presence of the transition or lanthanide reagent to form the protected substituted nucleosides (2a) or (2b). The reaction of Step (A) is carried out in an inert solvent. Suitable inert solvents which may be used include tetrahydrofuran, acetone, dioxane, chloroform, dichloromethane, ether, nitrobenzene, dimethylsulfoxide, 1,2-dichloroethane, 1,2-dimethoxyethane, toluene and acetonitrile and/or any combination thereof. Preferably the inert solvent is anhydrous. Reaction temperatures can be in the range of 0° C. to 130° C. Most conveniently, the reaction is carried out by mixing the reactants between −5° C. and 40° C., followed by heating in a sealed vessel at 40° C. to 115° C. Preferably, the reaction is carried out by heating the reactants between 60° C. and 95° C. Reaction times usually vary from about one hour to about twenty-four hours, but generally a maximum yield is obtained between three and six hours.

As stated above, X is a halogen but most preferably is fluorine. The substituted transition or lanthanide reagent MY may be selected from those of the formulae recited above. Particular reagents that may be used include samarium acetylacetonate, cerium acetylacetonate, samarium fluoride, terbium fluoride, dysprosium fluoride, yttrium fluoride, scandium fluoride or ytterbium fluoride.

As used herein, the term "halogen" means fluoro, chloro, bromo or iodo.

Advantageously, the reagent used is HF dissolved in a suitable inert solvent at molar ratios of 0.01 to 15%. HF may be dissolved advantageously in dioxane, 1,2-dimethoxyethane or tetrahydrofuran.

Hydroxy-protecting groups P, which are known to those skilled in the art, are desirable because they prevent side reactions and provide increased yields in later steps of the reaction sequence. Suitable hydroxy-protecting groups may be, for example, acyl groups such as benzyloxy-carbonyl, benzhydryloxycarbonyl, trityloxycarbonyl, p-nitro-benzyloxycarbonyl, pivaloyl, and 2,2,2-trichloroethoxycarbonyl, aralkyl groups such as benzyl, benzhydryl, trityl or p-nitrobenzyl or triorganosilyl groups such as tri($C_1$–$C_6$) alkylsilyl (e.g., trimethylsilyl, triethylsilyl, triisopropylsilyl, isopropyldimethylsilyl, t-butyldimethylsilyl, methyldiisopropylsilyl or methyldi-t-butylsilyl), triarylsilyl (e.g., triphenylsilyl, tri-p-xylylsilyl) or triaralkylsilyl (e.g., tribenzylsilyl). Examples of these and other suitable hydroxyprotecting groups such as methanesulfonyl, alkyl sulfonyl, aryl sulfonyl and methods for their formation and removal are known in the art, see e.g., Protective Groups in Organic Synthesis, T. W. Greene, John Wiley & Sons, New York, 1981, Chapter 2. The hydroxy-protecting group selected is preferably one that is easily removable in Step (B) of the reaction process.

The reaction of Step (B) in which the protecting group P is trityl is best performed with p-toluenesulfonic acid in methyl alcohol at ambient temperature from about one hour to about twenty-four hours, but generally a maximum yield is obtained between eighteen and twenty four hours.

Upon further study of the specification and appended claims, further objects and advantages of this invention will become apparent to those skilled in the art.

This invention will be described in greater detail in conjunction with the following, non-limiting, specific examples.

EXAMPLE 1

5'-0-Methanesulfonyl-2',3'-dideoxy-3'-fluorothymidine

To a suspension of 500 mg of 5'-0-methanesulfonyl-2'-deoxy-2,3'-anhydrothymidine in 10 ml of 7% HF-1,2-dimethoxyethane is added 1.5 g of samarium acetylacetonate. The reaction vessel is sealed and heated with stirring at 90° C. for 6 hours. To the resultant mixture is added 2 g of calcium carbonate and 20 ml of water. The mixture is stirred for 20 minutes then filtered through a pad of diatomaceous earth. The filtrate is evaporated to give 767.2 mg of solid. The sample is analyzed by HPLC using a spherisorb CN, 5 micron (250 mm×4.6 mm) column. A gradient of solution A:hexane and solution B:methylene chloride/ethanol/hexane (55:25:20) over 30 minutes at a flow rate of 1.5 ml/minute is used.

| Time | % A | % B |
| --- | --- | --- |
| 00.0 | 65.0 | 35.0 |
| 10.0 | 65.0 | 35.0 |
| 20.0 | 10.0 | 90.0 |
| 30.0 | 10.0 | 90.0 |

Additionally, CI mass spectroscopy (ammonia as carrier gas) is used and the M+NH$_4$ ion is observed at 340 a.m.u.

EXAMPLE 2

5'-0-Methanesulfonyl-2',3'-dideoxy-3'-fluorothymidine

The reaction is performed under the same conditions as Example 1 with 3.35 mM of samarium fluoride to give 450 mg of product.

EXAMPLE 3

5'-0-Methanesulfonyl-2',3'-dideoxy-3'-fluorothymidine

The reaction is performed under the same conditions as Example 1 with 3.35 mM of cerium acetylacetonate to give 745 mg of product.

EXAMPLE 4

5'-0-Methanesulfonyl-2',3'-dideoxy-3'-fluorothymidine

The reaction is performed under the same conditions as Example 1 with 3.35 mM of terbium fluoride to give 549 mg of product.

EXAMPLE 5

5'-0-Methanesulfonyl-2',3'-dideoxy-3'-fluorothymidine

The reaction is performed under the same conditions as Example 1 with 3.35 mM of dysprosium fluoride to give 565 mg of product.

EXAMPLE 6

5'-0-Methanesulfonyl-2',3'-dideoxy-3'-fluorothymidine

The reaction is performed under the same conditions as Example 1 with 3.35 mM of yttrium fluoride to give 568 mg of product.

EXAMPLE 7

5'-0-Methanesulfonyl-2',3'-dideoxy-3'-fluorothymidine

The reaction is performed under the same conditions as Example 1 with 3.35 mM of scandium fluoride to give 529 mg of product.

EXAMPLE 8

5'-0-Methanesulfonyl-2',3'-dideoxy-3'-fluorothymidine

The reaction is performed under the same conditions as Example 1 with 3.35 mM of ytterbium fluoride to give 581 mg of product.

We claim:

1. A process for preparing a compound of the Formula:

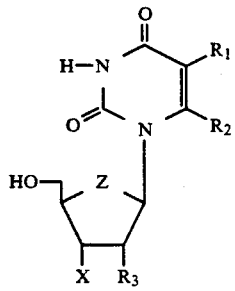

wherein Z is oxygen; $R_1$ and $R_2$ may be the same or different and are selected from the group consisting of hydrogen, lower alkyl and halogen, $R_3$ is selected from the group consisting of hydrogen and halogen; and X is a halogen; which comprises the steps of:

(a) mixing a compound of the formula:

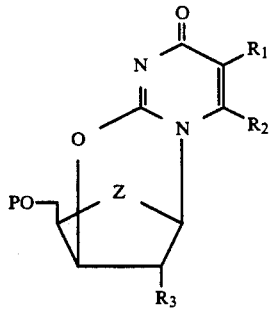

wherein P is selected from the group consisting of hydrogen, triphenylmethyl, methoxytriphenylmethyl, acetyl, pivaloyl, methanesulfonyl or trialkylsilyl with a reagent of the formula H—X wherein X is a halogen; in the presence of a reagent of the formula:

M—Y wherein M is selected from the group known as the transition or lanthanide metals; y is $(C_1-C_{10})$ branched or unbranched alkyl, or acetylacetonate, in an inert organic solvent, (b) heating said compound and reagents at 40°–115° C. for about one to 24 hours to produce a compound of the formula:

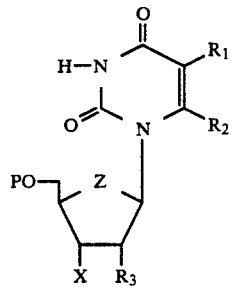

and, where P is other than hydrogen, (c) removing said protecting group.

2. A process for preparing a compound of the formula II:

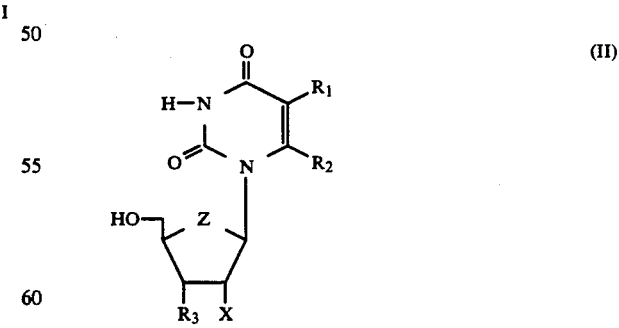

wherein Z is oxygen; $R_1$ and $R_2$ may be the same or different and are selected from the group consisting of hydrogen, lower alkyl and halogen, $R_3$ is selected from the group consisting of hydrogen and halogen; and X is a halogen; which comprises the steps of:

(a) mixing a compound of the formula:

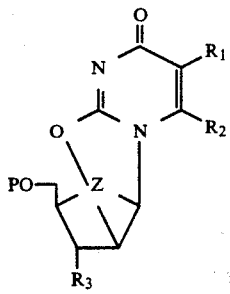

wherein P is hydrogen or a protecting group selected from the group consisting of triphenylmethyl, methoxytriphenylmethyl, acetyl, pivaloyl, methanesulfonyl or trialkylsilyl with a reagent of the formula H—X wherein X is a halogen; in the presence of a reagent of the formula:

M—Y wherein M is selected from the group known as the transition or lanthanide metals; y is ($C_1$-$C_{10}$) branched or unbranched alkyl, or acetylacetonate, in an inert organic solvent;

(b) heating said compound and reagents at 40°–115° C. for about one to 24 hours to produce a compound of the formula:

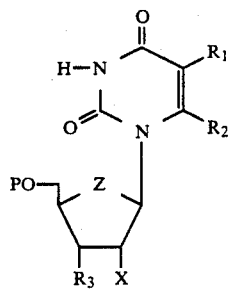

and, where P is other than hydrogen, (c) removing said protecting group.

3. A process according to claim 1 in which the reagent H—X is HF.

4. A process according to claim 2 in which the reagent H—X is HF.

5. A process according to claim 1 in which the reagent

M—Y is samarium acetylacetonate; wherein M is samarium and Y is 2,4-pentanedionate.

6. A process according to claim 1 in which the reagent

M—Y is cerium acetylacetonate; wherein M is cerium and Y is 2,4-pentanedionate.

7. A process according to claim 2 in which the reagent

M—Y is samarium and Y is 2,4-pentanedionate.

8. A process according to claim 2 in which the reagent

M—Y is cerium acetylacetonate; wherein M is cerium and Y is 2,4-pentanedionate.

9. A process according to claim 1 in which the inert organic solvent is selected from dioxane, tetrahydrofuran or dimethyoxyethane.

10. A process according to claim 2 in which the inert organic solvent is selected from dioxane, tetrahydrofuran or dimethoxyethane.

11. A process according to claim 1 in which the preferred temperature range is 60°–95° C.

12. A process according to claim 2 in which the preferred temperature range is 60°–95° C.

13. A process according to claim 1 in which the reagent HF is in a concentration of 0.01 to 15% in an ether solvent.

14. A process according to claim 2 in which the reagent HF is in a concentration of 0.01 to 15% in an ether solvent.

15. A process according to claim 1 in which the reagent HX is HF which is mixed with pyridine.

16. A process according to claim 2 in which the reagent HX is HF which is mixed with pyridine.

17. A process according to claim 15 in which the HF/pyridine concentration ratio is 70% HF to 30% pyridine.

18. A process according to claim 16 in which the HF/pyridine concentration ratio is 70% HF to 30% pyridine.

19. A process according to claim 1 in which ammonium hydrogen difluoride is added to the reaction mixture.

20. A process according to claim 2 in which ammonium hydrogen difluoride is added to the reaction mixture.

* * * * *